(12) United States Patent
McDonald et al.

(10) Patent No.: US 9,351,655 B2
(45) Date of Patent: May 31, 2016

(54) SYSTEMS, DEVICES, AND METHODS FOR ELECTRICALLY COUPLING TERMINALS TO ELECTRODES OF ELECTRICAL STIMULATION SYSTEMS

(75) Inventors: Matthew Lee McDonald, Glendale, CA (US); Anne Margaret Pianca, Santa Monica, CA (US); John Michael Barker, Ventura, CA (US); Aditya Vasudeo Pandit, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1666 days.

(21) Appl. No.: 12/545,264

(22) Filed: Aug. 21, 2009

(65) Prior Publication Data
US 2010/0057175 A1 Mar. 4, 2010

Related U.S. Application Data

(60) Provisional application No. 61/093,656, filed on Sep. 2, 2008.

(51) Int. Cl.
*A61B 5/042* (2006.01)
*A61N 1/05* (2006.01)
*H01R 24/58* (2011.01)
(Continued)

(52) U.S. Cl.
CPC ............ *A61B 5/0422* (2013.01); *A61N 1/0551* (2013.01); *H01R 24/58* (2013.01); *H01R 13/5224* (2013.01); *H01R 2107/00* (2013.01); *H01R 2201/12* (2013.01); *Y10T 29/49117* (2015.01)

(58) Field of Classification Search
USPC .................................. 607/119, 122, 114–117
See application file for complete search history.

(56) References Cited

U.S. PATENT DOCUMENTS

| 5,137,475 A | 8/1992 | Olms |
| 5,252,090 A | 10/1993 | Giurtino et al. |
| 5,374,285 A | 12/1994 | Vaiani et al. |

(Continued)

FOREIGN PATENT DOCUMENTS

| EP | 1651311 A1 | 5/2006 |
| EP | 1883449 A1 | 2/2008 |

(Continued)

OTHER PUBLICATIONS

U.S. Appl. No. 11/238,240, filed by Tom Xiaohai He on Sep. 29, 2005.

*Primary Examiner* — Catherine Voorhees
(74) *Attorney, Agent, or Firm* — Lowe Graham Jones PLLC; Bruce E. Black (57) ABSTRACT

An implantable lead includes a first lead assembly with a distal tip and a medial end, a medial section with a first end and a second end, and a first intermediate assembly disposed between the first lead assembly and the first end of the medial section. The first lead assembly includes a plurality of external contacts and at least one conductive wire disposed in the first lead assembly. The at least one conductive wire extends from at least one external contact towards the medial end of the first lead assembly. The medial section includes a plurality of conductors extending from the first end to the second end. The first intermediate assembly includes a plurality of conductive elements. At least one of the conductive elements is configured and arranged to electrically couple the at least one conductive wire to at least one of the conductors.

1 Claim, 9 Drawing Sheets

(51) Int. Cl.
  *H01R 13/52* (2006.01)
  *H01R 107/00* (2006.01)

(56) References Cited

U.S. PATENT DOCUMENTS

| | | | |
|---|---|---|---|
| 5,899,930 A | 5/1999 | Flynn et al. | |
| 5,906,634 A | 5/1999 | Flynn et al. | |
| 5,991,650 A | 11/1999 | Swanson et al. | |
| 6,181,969 B1 | 1/2001 | Gord | |
| 6,210,339 B1 | 4/2001 | Kiepen et al. | |
| 6,343,233 B1 | 1/2002 | Werner et al. | |
| 6,366,820 B1 | 4/2002 | Doan et al. | |
| 6,440,488 B2 | 8/2002 | Griffin, III et al. | |
| 6,516,227 B1 | 2/2003 | Meadows et al. | |
| 6,609,032 B1 | 8/2003 | Woods et al. | |
| 6,705,900 B2 | 3/2004 | Sommer et al. | |
| 6,741,892 B1 | 5/2004 | Meadows et al. | |
| 6,757,970 B1 | 7/2004 | Kuzma et al. | |
| 6,799,991 B2 | 10/2004 | Williams et al. | |
| 6,847,845 B2 | 1/2005 | Belden | |
| 6,980,863 B2 | 12/2005 | van Venrooij et al. | |
| 7,027,862 B2 | 4/2006 | Dahl et al. | |
| 7,039,470 B1 | 5/2006 | Wessman | |
| 7,047,081 B2 | 5/2006 | Kuzma | |
| 7,047,627 B2 | 5/2006 | Black et al. | |
| 7,164,951 B2 | 1/2007 | Ries et al. | |
| 7,225,034 B2 | 5/2007 | Ries et al. | |
| 7,322,832 B2 | 1/2008 | Kronich et al. | |
| 7,337,003 B2 | 2/2008 | Malinowski | |
| 2003/0045911 A1 | 3/2003 | Bruchmann et al. | |
| 2003/0114905 A1 | 6/2003 | Kuzma | |
| 2003/0120327 A1 | 6/2003 | Tobritzhofer et al. | |
| 2003/0199948 A1 | 10/2003 | Kokones et al. | |
| 2004/0059392 A1 | 3/2004 | Parramon et al. | |
| 2004/0215282 A1 | 10/2004 | Weijden et al. | |
| 2005/0043770 A1 | 2/2005 | Hine et al. | |
| 2005/0043771 A1 | 2/2005 | Sommer et al. | |
| 2005/0107859 A1 | 5/2005 | Daglow et al. | |
| 2005/0113899 A1 | 5/2005 | Cross | |
| 2005/0165465 A1 | 7/2005 | Pianca et al. | |
| 2005/0222658 A1 * | 10/2005 | Hoegh et al. | 607/116 |
| 2006/0089698 A1 * | 4/2006 | Sundberg et al. | 607/122 |
| 2007/0027512 A1 | 2/2007 | Chan et al. | |
| 2007/0027513 A1 | 2/2007 | Chan et al. | |
| 2007/0100387 A1 | 5/2007 | Gerber | |
| 2007/0150007 A1 | 6/2007 | Anderson et al. | |
| 2007/0150036 A1 | 6/2007 | Anderson | |
| 2007/0161294 A1 | 7/2007 | Brase et al. | |
| 2007/0219595 A1 | 9/2007 | He | |
| 2007/0239243 A1 | 10/2007 | Moffitt et al. | |
| 2008/0027524 A1 | 1/2008 | Maschino et al. | |
| 2008/0077190 A1 | 3/2008 | Kane et al. | |
| 2008/0262564 A1 | 10/2008 | Alexander et al. | |
| 2008/0262582 A1 | 10/2008 | Alexander et al. | |
| 2008/0262585 A1 | 10/2008 | Alexander et al. | |
| 2009/0005823 A1 | 1/2009 | Pianca et al. | |
| 2009/0012591 A1 | 1/2009 | Barker | |
| 2009/0054941 A1 * | 2/2009 | Eggen et al. | 607/9 |
| 2009/0112272 A1 | 4/2009 | Schleicher et al. | |
| 2009/0171421 A1 * | 7/2009 | Atalar et al. | 607/63 |
| 2009/0234368 A1 * | 9/2009 | Gore | 606/129 |
| 2009/0234405 A1 | 9/2009 | Sommer et al. | |
| 2009/0248095 A1 * | 10/2009 | Schleicher et al. | 607/2 |
| 2009/0248111 A1 | 10/2009 | Pianca et al. | |
| 2009/0248122 A1 * | 10/2009 | Pianca | 607/115 |
| 2009/0248124 A1 * | 10/2009 | Pianca et al. | 607/116 |
| 2009/0254162 A1 * | 10/2009 | Quinci et al. | 607/115 |
| 2009/0264780 A1 | 10/2009 | Schilling | |
| 2010/0042109 A1 * | 2/2010 | Barker | 606/129 |
| 2011/0172606 A1 * | 7/2011 | Olson | 604/174 |

FOREIGN PATENT DOCUMENTS

| | | |
|---|---|---|
| WO | 03063946 A2 | 8/2003 |
| WO | WO 03063946 A2 * | 8/2003 |
| WO | 2005102447 A1 | 11/2005 |
| WO | 2007047966 A2 | 4/2007 |
| WO | 2007059343 A2 | 5/2007 |

* cited by examiner

SYSTEMS, DEVICES, AND METHODS FOR ELECTRICALLY COUPLING TERMINALS TO ELECTRODES OF ELECTRICAL STIMULATION SYSTEMS

CROSS-REFERENCE TO RELATED APPLICATIONS

This application is a utility patent application based on a previously filed U.S. Provisional Patent Application Ser. No. 61/093,656 filed on Sep. 2, 2008, the benefit of which is hereby claimed under 35 U.S.C. §119(e) and incorporated herein by reference.

FIELD

The present invention is directed to the area of implantable electrical stimulation systems and methods of making and using the systems. The present invention is also directed to implantable electrical stimulation leads (and lead extensions) and methods of electrically coupling electrodes (or conductive contacts) to terminals of the lead (or lead extension), as well as making and using the leads (and lead extensions) and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable lead includes a first lead assembly with a distal tip and a medial end, a medial section with a first end and a second end, and a first intermediate assembly disposed between the first lead assembly and the first end of the medial section. The first lead assembly includes a plurality of external contacts and at least one conductive wire disposed in the first lead assembly. The at least one conductive wire extends from at least one external contact towards the medial end of the first lead assembly. The medial section includes a plurality of conductors extending from the first end to the second end. The first intermediate assembly includes a plurality of conductive elements. At least one of the conductive elements is configured and arranged to electrically couple the at least one conductive wire of the first lead assembly to at least one of the conductors at the first end of the medial section.

In another embodiment, an electrical stimulating system includes an implantable lead, a second intermediate assembly, a control module, and a connector. The implantable lead includes a first lead assembly with a distal tip and a medial end, a medial section with a first end and a second end, and a first intermediate assembly disposed between the first lead assembly and the first end of the medial section. The first lead assembly includes a plurality of external contacts and at least one conductive wire disposed in the first lead assembly. The at least one conductive wire extends from at least one external contact towards the medial end of the first lead assembly. The medial section includes a plurality of conductors extending from the first end to the second end. The first intermediate assembly includes a plurality of conductive elements. At least one of the conductive elements is configured and arranged to electrically couple the at least one conductive wire of the first lead assembly to at least one of the conductors at the first end of the medial section. The second intermediate assembly is electrically coupled to the second end of the medial section via an intermediate section. The control module is configured and arranged to electrically couple to the first proximal end and the at least one second proximal end. The control module includes a housing and an electronic subassembly disposed in the housing. The connector has a proximal end, a distal end, and a longitudinal length. The connector is configured and arranged to receive the lead. The connector includes a connector housing and a plurality of connector contacts disposed in the connector housing. The connector housing defines a port at the distal end of the connector. The port is configured and arranged for receiving the proximal end of the lead. The connector contacts are configured and arranged to couple to at least one of the plurality of terminals disposed on the proximal end of the lead.

In yet another embodiment, a method for making an implantable lead includes disposing at least one conductor with a first end and a second end along a medial section of the lead and disposing at least one conductive wire along a first lead assembly from an external contact disposed on the first lead assembly to a medial end of the first lead assembly. The method also includes electrically coupling the first end of the at least one conductor to a conductive element disposed in a first intermediate assembly and electrically coupling the at least one conductive element disposed in the first intermediate assembly to the conductive wire disposed in the first lead assembly.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads (and lead extensions) and methods of electrically coupling electrodes (or conductive contacts) to terminals of the lead (or lead extension), as well as making and using the leads (and lead extensions) and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
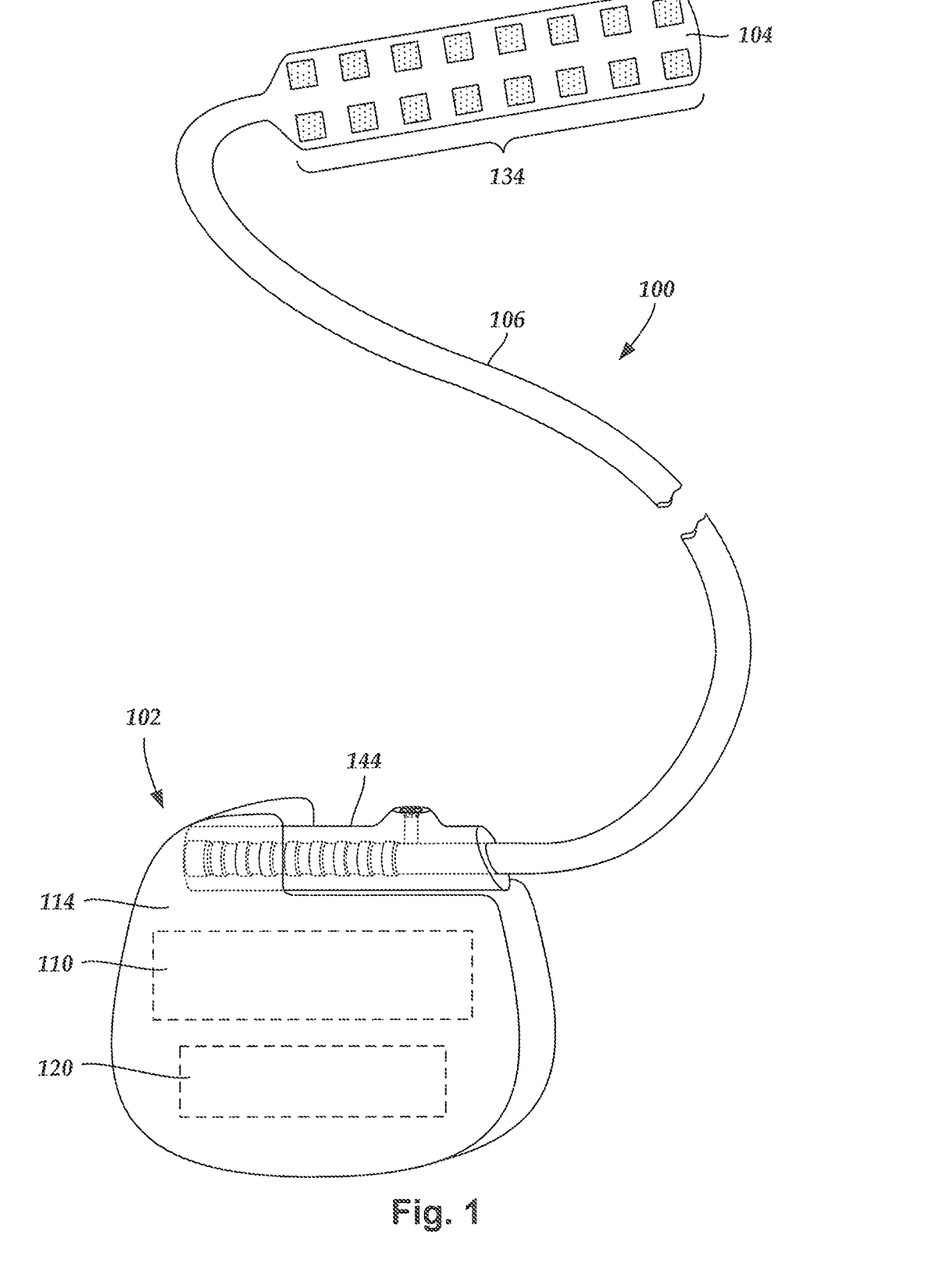
FIG. 1 is a schematic view of one embodiment of an electrical stimulation system, according to the invention.
Figure 2:
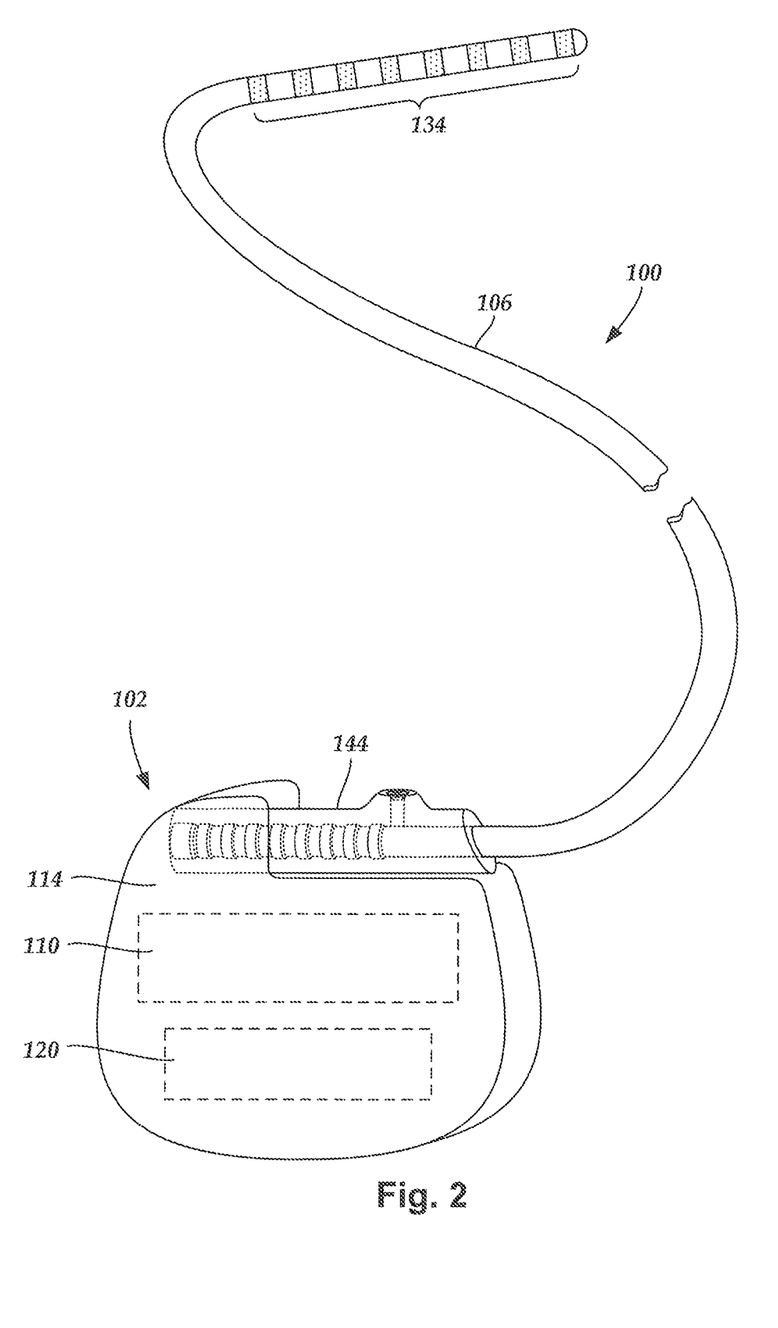
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 324 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, a trial stimulation cable, or an adaptor). Conductors (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. There may also be one or more lumens (not shown) that open at, or near, the proximal end of the lead, for example, for inserting a stylet rod to facilitate placement of the lead within an body of a patient.

Figure 3A:
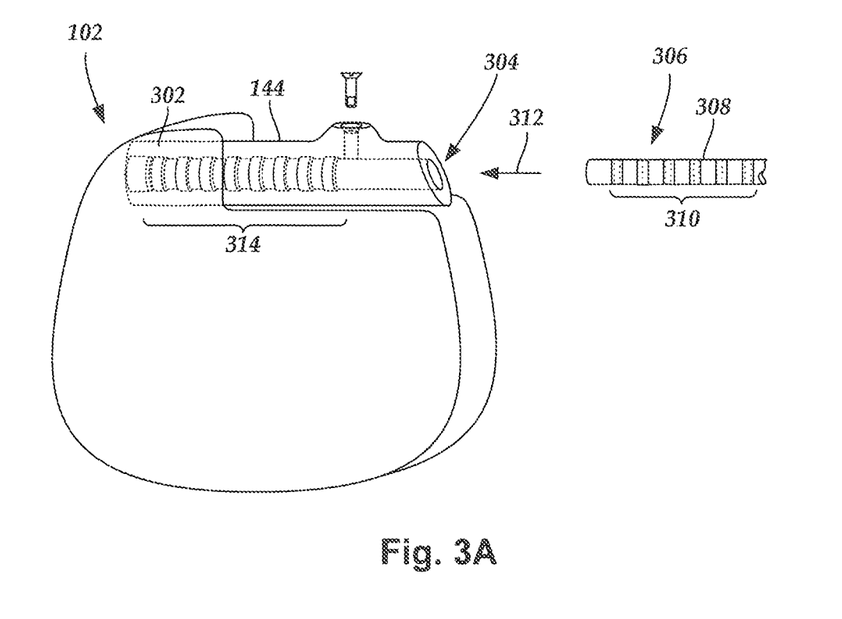
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
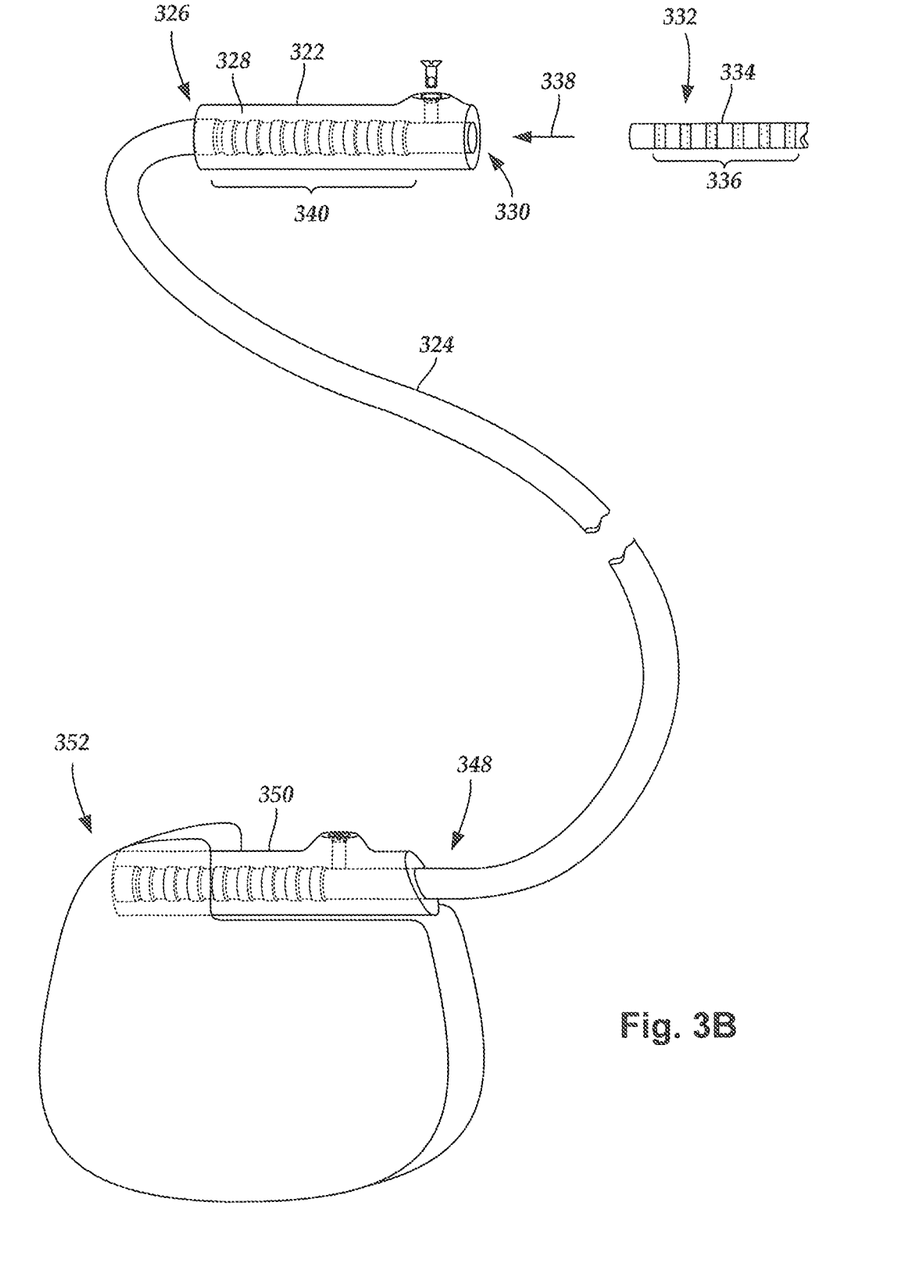
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

One or more of the conductors connecting at least one electrode (or conductive contact) to a terminal can be arranged in a conductor path to eliminate or reduce the effect of RF irradiation, such as that generated during magnetic resonance imaging ("MRI"). In at least some embodiments, a conductor path includes forming one or more layers of helical coils. One challenge with implementing multi-layered, coiled conductors ("conductors") in the lead (or lead extension) is coupling the ends of the conductors to electrodes (or conductive contacts) and terminals. It will be understood that the arrangements described herein can be used in circumstances other than when the conductors are coiled.

In at least some embodiments, the lead (or lead extension) includes at least one lead assembly coupled to one end of a medial section. In at least some embodiments, the medial section includes one or more helical coils of conductors disposed over an inner core. In some embodiments, the lead assembly includes a plurality of external contacts. In at least some embodiments, the external contacts are electrodes disposed on the lead. In at least some embodiments, the electrodes are separated from one another by non-conductive spacers assembled over an ablated section at one end of the inner core. In at least some embodiments, the external contacts are terminals disposed on the lead. In at least some embodiments, the terminals are separated from one another by non-conductive spacers assembled over another ablated section at one end of the inner core. In at least some embodiments, the lead assembly with electrodes may be disposed at one end of the medial section and the lead assembly with terminals may be disposed at the opposite end of the medial section.

Likewise, a lead extension may also include one or two lead assemblies electrically coupled to a medial section that includes a plurality of conductors extending along an inner core. Typically, lead extensions include conductive contacts at a distal end instead of electrodes. Accordingly, the lead assemblies for lead extension generally include either conductive contacts or terminals.

Figures 4, 5A:
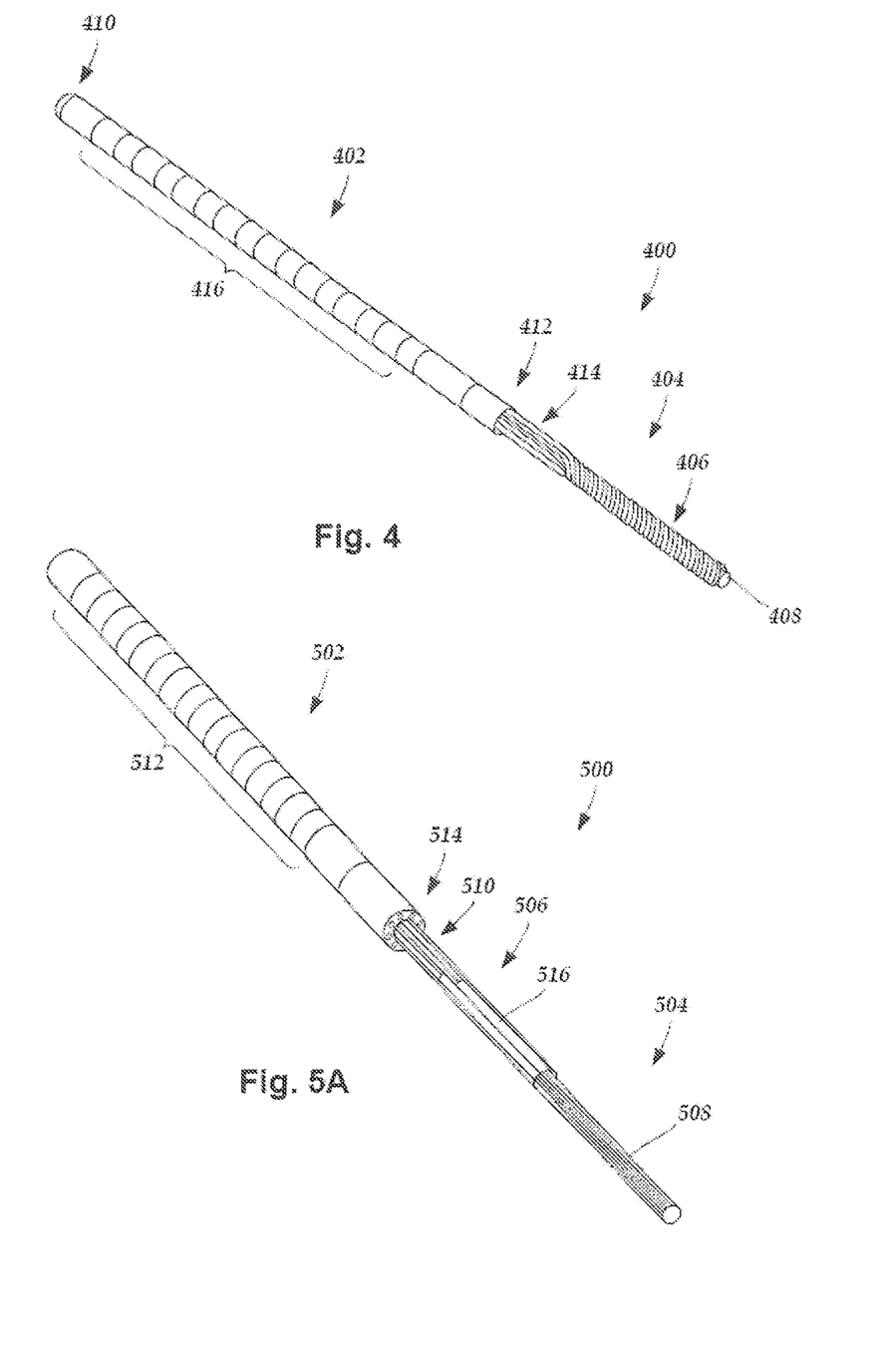
FIG. 4 is a schematic perspective view of one embodiment of a lead assembly of a lead electrically coupled to a portion of a medial section of the lead, the medial section including a plurality of partially-uncoiled conductors, the lead assembly including a plurality of lumens into which the uncoiled ends of the conductors are inserted, according to the invention.
FIG. 5A is a schematic perspective view of one embodiment of a lead assembly of a lead coupled to a portion of a medial section of the lead via an intermediate assembly, the intermediate assembly including conductive tracings disposed on a substantially-tubular non-conductive substrate, the lead assembly including conductive wires electrically coupled to the conductive tracings, the medial section including an inner core mechanically coupled to the non-conductive substrate, according to the invention.

FIG. 4 is a schematic perspective view of one embodiment of a lead assembly 402 of a lead (or lead extension) 400 electrically coupled to a portion of a medial section 404 of the lead (or lead extension) 400. In FIG. 4, and in subsequent figures, the medial section 404 of the lead (or lead extension) 400 is shown without an outer covering for clarity of illustration. In FIG. 4, the medial section 404 includes a plurality of conductors 406 at least partially disposed over an inner core 408. The plurality of conductors 406 are partially uncoiled at the end and electrically coupled to the lead assembly 402.

In at least some embodiments, the lead assembly 402 has a distal tip 410 and a medial end 412. The lead assembly 402 defines a plurality of lumens 414 into which the uncoiled ends of the conductors 406 may be inserted. In at least some embodiments, each of the conductors 406 can be extended along the length of one of the lumens 414 to an external contact 416 and electrically coupled to the external contact 416. It will be understood that the arrangements described herein may also be compatible with leads including one or more non-coiled conductors.

Conductors 406 may be electrically coupled to external contacts 416 using many different techniques including, for example, welding, soldering, bonding, adhesive, conductive fasteners, mechanical interference, and the like or combinations thereof. In at least some embodiments, the lead assembly 402 may be permanently or removably coupled to the medial section 404. In at least some embodiments, one or more finished joints between the lead assembly 402 and the medial section 404 may be sealed to maintain an isodiametric profile along a longitudinal length of the lead (or lead extension) 400. The finished joints may be sealed using many different techniques including, for example, over-molding, over-flowing, and the like or combinations thereof.

In at least some embodiments, an intermediate assembly may be used to facilitate the electrical coupling of the lead assembly to the medial section. In at least some embodiments, the intermediate assembly includes one or more conductive elements. In at least some embodiments, the intermediate assembly includes one or more conductive elements disposed on a non-conductive member. For example, in at least some embodiments conductive tracings disposed on a non-conductive substrate may be used to facilitate the electrical coupling of the lead assembly to the medial section.

FIG. 5A is a schematic perspective view of one embodiment of a lead assembly 502 of a lead (or lead extension) 500 coupled to a portion of a medial section 504 of the lead (or lead extension) 500 via an intermediate assembly 506. The medial section 504 includes an inner core 508. The lead assembly 502 includes a plurality of conductive wires 510 each electrically coupled to at least one external contact 512 and extending towards a medial end 514.

The intermediate assembly 506 includes a substantially tubular-shaped, non-conductive substrate 516 ("substrate"). In FIG. 5A, the substrate 516 is shown coupled to the inner core 508. In some embodiments, the substrate 516 is permanently coupled to the inner core 508. In other embodiments, the substrate 516 is removably coupled to the inner core 508. In at least some embodiments, the substrate 516 is configured and arranged to be disposed over at least a portion of the inner core 508. In at least some embodiments, the lead assembly 502 defines a lumen (not shown) configured and arranged for receiving one end of the inner core 508. The substrate 516 may be coupled to the inner core 508 in many different ways including, for example, one or more adhesives, an interference fit, overmolding, and the like or combinations thereof.

Figures 5B, 5C:
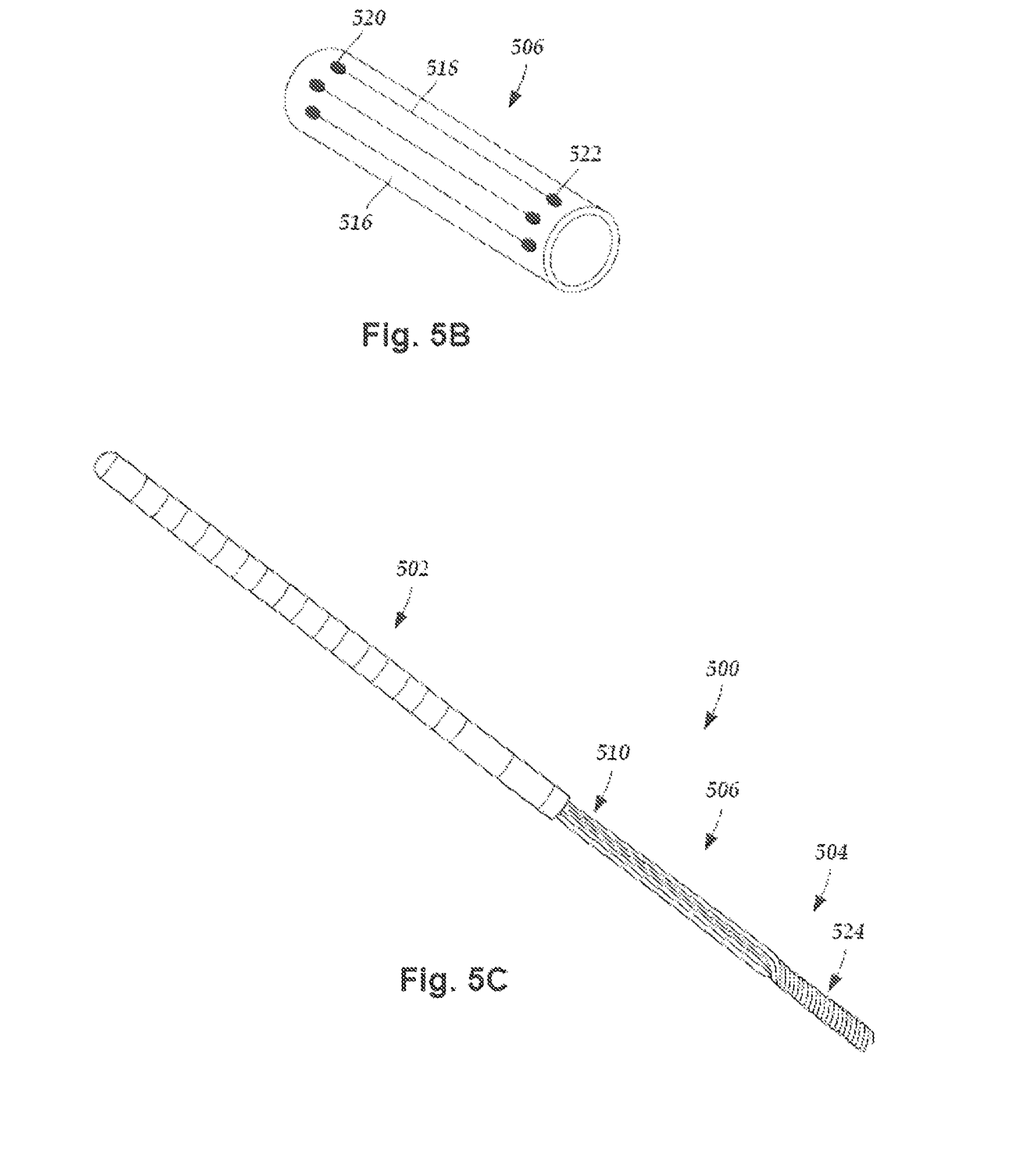
FIG. 5B is a schematic perspective view of one embodiment of an intermediate assembly that includes conductive tracings disposed on a substantially tubular, non-conductive substrate, according to the invention.
FIG. 5C is a schematic side view of one embodiment of the lead assembly of the lead shown in FIG. 5A electrically coupled to the portion of the medial section of the lead shown in FIG. 5A via the intermediate assembly shown in FIG. 5A, the intermediate assembly including conductive tracings disposed on a substantially-tubular non-conductive substrate, the lead assembly including conductive wires electrically coupled to the conductive tracings, the medial section including partially-uncoiled conductors also electrically coupled to the conductive tracings, according to the invention.

FIG. 5B shows one embodiment of the intermediate assembly 506. The intermediate assembly 506 includes the substrate 516. The substrate 516 includes conductive tracings, such as conductive trace 518, disposed on the substrate 516. The conductive tracings electrically couple at least one lateral conductive pad, such as lateral conductive pad 520, to at least one medial conductive pad, such as medial conductive pad 522. In at least some embodiments, the conductive tracings are disposed on an exterior surface of the substrate 516. In other embodiments, the conductive tracings are disposed on an interior surface of the substrate 516. In at least some embodiments, the lateral conductive pads are configured and arranged to electrically couple with the conductive wires (510 in FIG. 5A) and the medial conductive pads are configured and arranged to electrically couple with the conductors (524 of FIG. 5C).

FIG. 5C is a schematic side view of one embodiment of the conductive wires 510 of the lead assembly 502 electrically coupled to a plurality of partially-uncoiled conductors 524 of the medial section 504 via the intermediate assembly 506. In at least some embodiments, the conductors 524 are at least partially disposed over the inner core 508 of the medial section 504. In FIG. 5C, the conductors 524 are shown uncoiled at one end and electrically coupled to the exposed conductive surfaces of the substrate (516 of FIG. 5A). The conductors 524 may be electrically coupled to the exposed conductive surfaces of the substrate (516 of FIG. 5A) using many different techniques including, for example, welding, soldering, bonding, adhesive, conductive fasteners, mechanical interference, and the like or combinations thereof. It will be understood that the arrangements described herein may also be compatible with leads (or lead extensions) that include one or more non-coiled conductors.

Figure 5D:
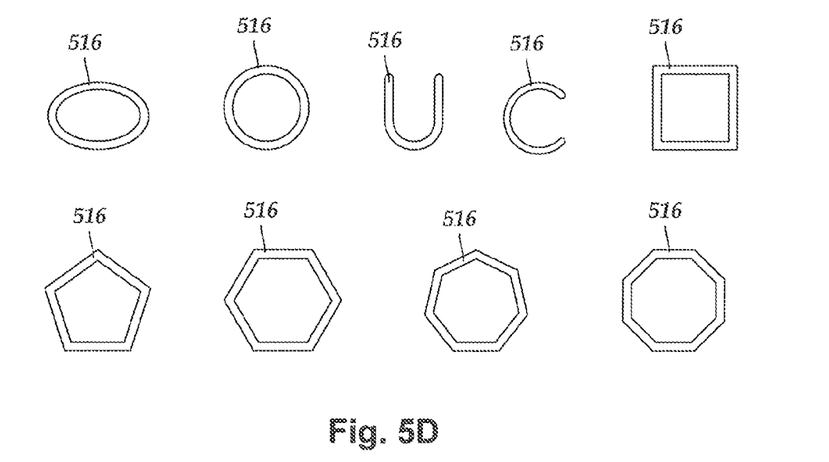
FIG. 5D is a schematic transverse cross-sectional view of several different exemplary embodiments of the intermediate assembly of FIG. 5A, according to the invention.

In FIG. 5C, the substrate 516 is shown as having a rounded transverse cross-sectional shape. As shown in FIG. 5D, in at least some embodiments the transverse cross-sectional shape of the substrate 516 is circular, oval, U-shaped, C-shaped, or the like. In at least some embodiments, the exterior surface of the substrate 516 includes one or more faces that are flat, or substantially flat, to facilitate electrical coupling. For example, as shown in FIG. 5D the substrate 516 may have a transverse cross-sectional shape that is rectangular, pentagonal, hexagonal, heptagonal, octagonal, or the like. It will be understood that the substrate 516 may have a transverse cross-section shape with other numbers of faces including, for example, nonagonal, decagonal, and the like. As will be understood, other numbers of faces may be used as well. In at least some embodiments, the number of faces of the substrate 516 is proportional to the number of conductive wires 510. In at least some embodiments, the number of faces of the substrate 516 is equal to the number of conductive wires 510. In some embodiments, the faces extend the longitudinal length of the substrate 516. In other embodiments, one or more of the faces extend for only a portion of the longitudinal length of the substrate 516.

In some embodiments, the substrate 516 is a substantially-tubular printed circuit board. In other embodiments, the substrate 516 is a printed flex circuit. In at least some embodiments, the printed flex circuit is printed flat and then rolled or bent into a desired shape, such as the shapes described above with reference to FIG. 5A. In some embodiments, the conductors 524 may be electrically coupled to the printed flex circuit before the printed flex circuit is rolled or bent into the desired shape. In other embodiments, the conductors 524 may be electrically coupled to the printed flex circuit after the printed flex circuit is rolled or bent into the desired shape.

In at least some embodiments, the lead assembly 502 may be permanently or removably attached to the intermediate assembly 506. In at least some embodiments, the medial section 504 may be permanently or removably attached to the intermediate assembly 506. In at least some embodiments, one or more finished joints between the lead assembly 502, the intermediate assembly 506, and the medial section 504 may be sealed to maintain an isodiametric profile along a longitudinal length of the lead (or lead assembly) 500. The finished joints may be sealed using many different techniques including, for example, over-molding, over-flowing, and the like or combinations thereof.

Figure 6:
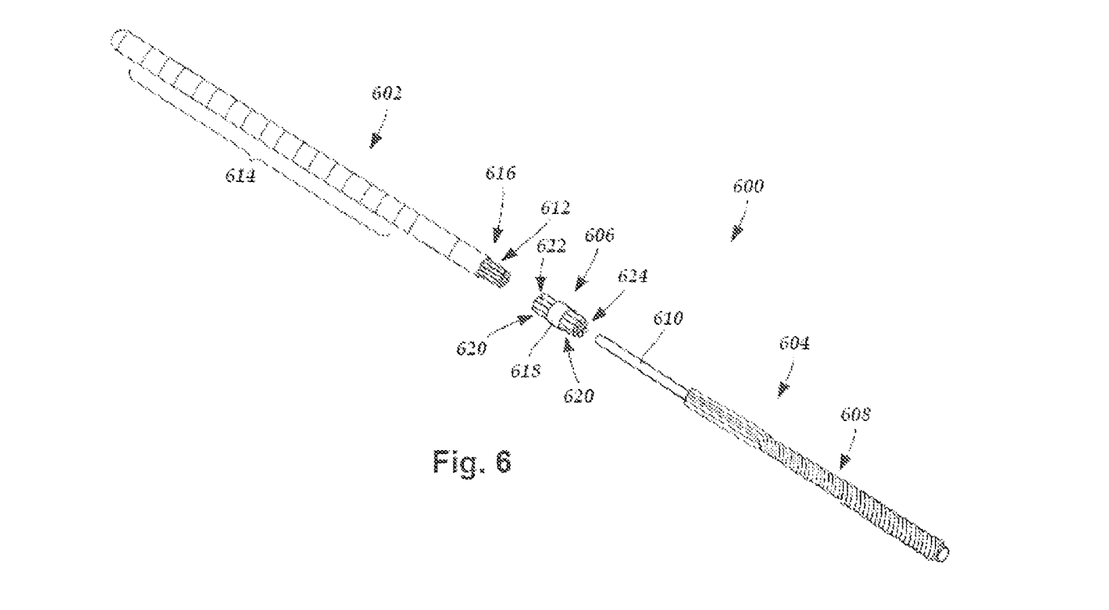
FIG. 6 is a schematic perspective exploded view of one embodiment of a lead assembly of a lead with conductive wires extending from a medial end of the lead assembly, a portion of a medial section of the lead, the medial section including a plurality of partially-uncoiled conductors disposed over an inner core, and an intermediate assembly, the intermediate assembly including a non-conductive housing and a plurality of conductive members, the non-conductive housing configured and arranged for mechanically coupling to the inner core, the conductive members each configured and arranged for electrically coupling to one of the conductive wires and to one of the partially-uncoiled conductors, according to the invention.

In at least some embodiments, the intermediate assembly may include one or more conductive members disposed in a non-conductive housing. FIG. 6 is a schematic perspective exploded view of one embodiment of a lead assembly 602 of a lead (or lead extension) 600 configured and arranged for electrical coupling to a portion of a medial section 604 of the lead (or lead extension) 600 via an intermediate assembly 606. The medial section 604 includes a plurality of partially-uncoiled conductors 608 at least partially disposed over an inner core 610. The lead assembly 602 includes conductive wires 612 electrically coupled to a plurality of external contacts 614 and extending towards a medial end 616 of the lead assembly 602. It will be understood that the arrangements described herein may also be compatible with leads including one or more non-coiled (or partially uncoiled) conductors.

The intermediate assembly 606 includes a non-conductive housing 618 and a plurality of conductive members 620 disposed in the non-conductive housing 618. In at least some embodiments, the non-conductive housing 618 is substantially tubular. In at least some embodiments, the non-conductive housing 618 is coupled to the inner core 610. In some embodiments, the non-conductive housing 618 is permanently coupled to the inner core 610. In other embodiments, the non-conductive housing 618 is removably coupled to the inner core 610. In at least some embodiments, the non-conductive housing 618 is configured and arranged to be disposed over at least a portion of the inner core 610. In at least some embodiments, the lead assembly 602 defines a lumen (not shown) configured and arranged for receiving one end of the inner core 610.

In FIG. 6, the conductive members 620 are shown as substantially tubular and having a rounded transverse cross-sectional shape. In at least some embodiments, the transverse cross-sectional shape of the conductive members 620 are circular, oval, U-shaped, C-shaped, or the like. In at least some embodiments, the exterior surface of the conductive members 620 includes one or more faces. For example, the conductive members 620 may have a transverse cross-sectional shape that is rectangular, pentagonal, hexagonal, heptagonal, octagonal, nonagonal, decagonal, and the like. As will be understood, other numbers of faces may be used as well. In at least some embodiments, the number of faces of the conductive members 620 is proportional to the number of conductive wires 612. In at least some embodiments, the number of faces of the conductive members 620 is equal to the number of conductive wires 612. In some embodiments, the faces extend the longitudinal length of the conductive members 620. In other embodiments, one or more of the faces extend for only a portion of the longitudinal length of the conductive members 620.

In at least some embodiments, the conductive members 620 are arranged along the perimeter of the non-conductive housing 618. In at least some embodiments, the conductive members 620 are arranged along the perimeter of the non-conductive housing 616 in a pattern that electrically isolates each conductive member 620 from one another. In at least some embodiments, the conductive members 620 are arranged along the perimeter of the non-conductive housing 618 in a pattern that approximates the positioning of the conductive wires 612 extending from the medial end 616 of the lead assembly 602. In at least some embodiments, the conductive members 620 are arranged along the perimeter of the non-conductive housing 618 so that an approximately equal length of each conductive member 620 extends from opposing ends of the non-conductive housing 618.

In at least some embodiments, each of the conductive members 620 are configured and arranged for electrically coupling the conductive wires 612 of the lead assembly 602 to the conductors 608 of the medial section 604. In at least some embodiments, a first end 622 of each conductive member 620 is configured and arranged to receive one or more conductive wires 612 of the lead assembly 602. In at least some embodiments, a second end 624 of each conductive member 620 is configured and arranged to receive one or more conductors 608 of the medial section 604. The conductive wires 612 or the conductors 608 may be electrically coupled to the conductive members 620 using many different techniques including, for example, welding, soldering, bonding, crimping, adhesive, and the like or combinations thereof. In at least some embodiments, the first end 622 and the second end 624 of at least one of the conductive members 620 are formed from two or more electrically coupled conductive elements. In at least some embodiments, at least one of the conductive members 620 is a hypo tube.

In at least some embodiments, the lead assembly 602 may be permanently or removably attached to the intermediate assembly 606. In at least some embodiments, the medial section 604 may be permanently or removably attached to the intermediate assembly 606. In at least some embodiments, one or more finished joints between the lead assembly 602, the intermediate assembly 606, and the medial section 604 may be sealed to maintain an isodiametric profile along a longitudinal length of the lead (or lead extension) 600. A finished joint may be sealed using many different techniques including, for example, over-molding, over-flowing, and the like or combinations thereof.

Figure 7A:
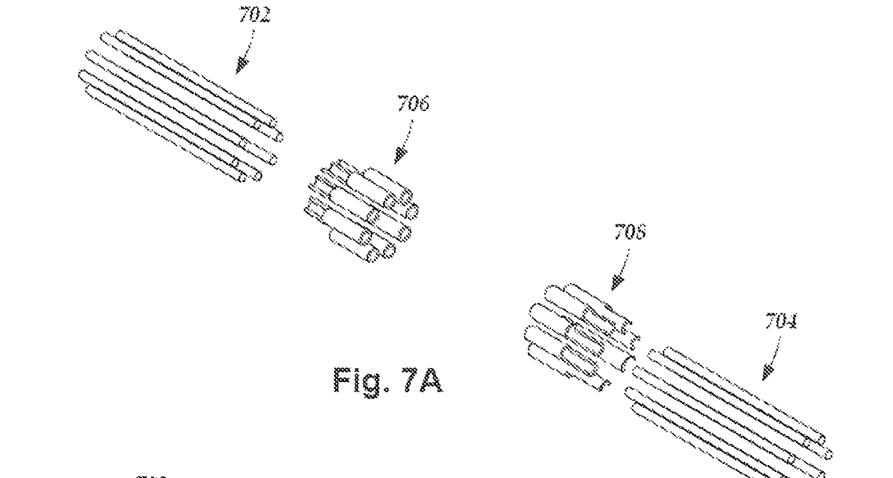
FIG. 7A is a schematic perspective exploded view of one embodiment of portions of conductive wires of a lead assembly of a lead, portions of conductors of a medial section of the lead, and two sets of conductive members, the first set of conductive members each configured and arranged for electrically coupling with one end of one of the conductive wires, and the second set of conductive members each configured and arranged for electrically coupling with one end of one of the conductors, according to the invention.
Figure 7B:
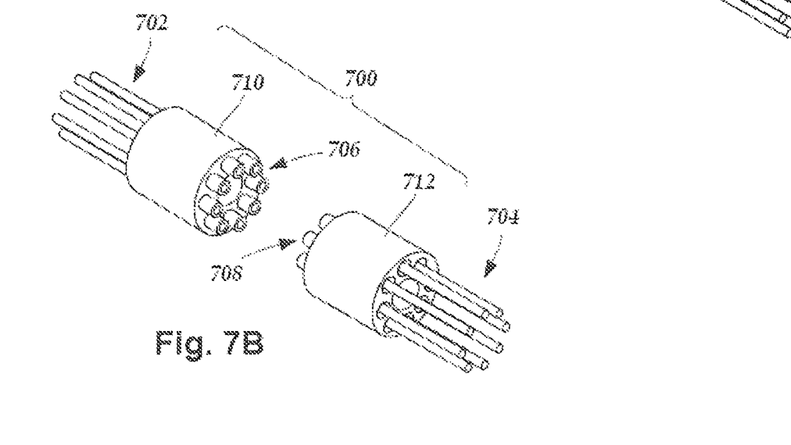
FIG. 7B is a schematic perspective exploded view of one embodiment of each of the first set of conductive members of FIG. 7A electrically coupled to one of the conductive wires of FIG. 7A and each of the second set of conductive members of FIG. 7A electrically coupled to one of the conductors of FIG. 7A, the first set and the second set of conductive members are each inserted into a separate non-conductive housing such that the tips of each of the first set and the second set of conductive members is exposed, according to the invention.
Figure 7C:
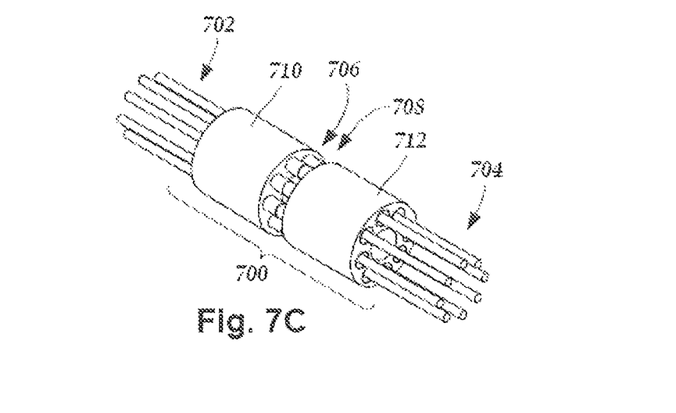
FIG. 7C is a schematic perspective view of one embodiment of the exposed tips of each of the first set of conductive members shown in FIG. 7B electrically coupled to one of the exposed tips of the second set of conductive members shown in FIG. 7B, according to the invention.

In at least some embodiments, the intermediate assembly may include a plurality of non-conductive members. FIG. 7A-7C illustrate one embodiment of steps for electrically coupling a lead assembly to a medial section via a plurality of non-conductive members. FIG. 7A is a schematic perspective exploded view of one embodiment of conductive wires 702 of a lead assembly (e.g., 602 of FIG. 6), conductors 704 of a medial section (e.g., 604 of FIG. 6), a first set of conductive members 706, and a second set of conductive members 708. Each of the first set of conductive members 706 is configured and arranged for electrically coupling with one end of one of the conductive wires 702, and each of the second set of conductive members 708 is each configured and arranged for electrically coupling with one end of one of the conductors 704.

In at least some embodiments, the conductive members 706 and 708 are substantially tubular shaped. In at least some embodiments, at least one of the conductive members 706 and 708 is a hypo tube. The conductive conductors 702 or the conductive wires 704 may be electrically coupled to the conductive members 706 or 708, respectively, using many different techniques including, for example, welding, soldering, bonding, crimping, adhesive, and the like or combinations thereof.

FIG. 7B is a schematic perspective exploded view of one embodiment of the conductive wires 702 electrically coupled to the conductors 704 via an intermediate assembly 700. In FIG. 7B, each of the first set of conductive members 706 is electrically coupled to one of the conductive wires 702. Likewise, each of the second set of conductive members 708 is electrically coupled to one of the conductors 704. Each of the first set of conductive members 706 is inserted into a non-conductive housing 710. Likewise, each of the second set of conductive members 708 is inserted into a non-conductive housing 712. In at least some embodiments, the sets of conductive members 706 and 708 are disposed in the non-conductive housings 710 and 712, respectively, such that one end of each conductive member of the first set of conductive members 706 and one end of each conductive member of the second set of conductive members 708 extends through a far end of the non-conductive housings 710 and 712, respectively, as shown in FIG. 7B.

In at least some embodiments, the non-conductive housings 710 and 712 are substantially tubular. In at least some embodiments, at least one of the non-conductive housings 710 and 712 are coupled to the inner core (e.g., 610 of FIG. 6). In some embodiments, at least one of the non-conductive housings 710 and 712 are permanently coupled to the inner core (e.g., 610 of FIG. 6). In other embodiments, at least one of the non-conductive housings 710 and 712 are removably coupled to the inner core (e.g., 610 of FIG. 6). In at least some embodiments, at least one of the non-conductive housings 710 and 712 is configured and arranged to be disposed over at least a portion of the inner core (e.g., 610 of FIG. 6).

In at least some embodiments, the conductive members 706 and 708 are arranged along the perimeter of at least one of the non-conductive housings 710 and 712. In at least some embodiments, at least some of the conductive members 706 and 708 are arranged along the perimeter of at least one of the non-conductive housings 710 and 712 in a pattern that electrically isolates at least some of the conductive member 706 and 708 from one another. In at least some embodiments, at least some of the conductive members 706 and 708 are arranged along the perimeter of at least one of the non-conductive housings 706 and 708 in a pattern that approximates the positioning of the conductive wires 702 extending from the medial end (e.g., 614 of FIG. 6) of the lead assembly (e.g., 602 of FIG. 6). In at least some embodiments, at least some of the conductive members 706 are arranged along the perimeter of the non-conductive housing 706 in a pattern that approximates the arrangement of the conductive members 708 along the perimeter of the non-conductive housing 708.

In at least some embodiments, the exposed ends of each conductive member of the first set of conductive members 706 that extends through the far end of the non-conductive housing 710 can be electrically coupled to the exposed ends of at least one conductive member of the second set of conductive members 708 that extends through the far end of the non-conductive housing 712. FIG. 7C is a schematic perspective view of one embodiment of the exposed ends of each of the first set of conductive members 706 of the intermediate assembly 700 electrically coupled to one of the exposed ends of each of the second set of conductive members 708. Each of the first set of conductive members 706 may be electrically coupled to one of the second set of conductive members 708 using many different techniques including, for example, welding, soldering, bonding, crimping, adhesive, and the like or combinations thereof.

In at least some embodiments, the lead assembly (e.g., 602 of FIG. 6) may be permanently or removably attached to the intermediate assembly 700. In at least some embodiments, the medial section (e.g., 604 of FIG. 6) may be permanently or removably attached to the intermediate assembly 700. In at least some embodiments, one or more finished joints between the lead assembly (e.g., 602 of FIG. 6), the intermediate assembly 700, and the medial section (e.g., 604 of FIG. 6) may be sealed to maintain an isodiametric profile along a longitudinal length of the lead (or lead extension) (e.g., 600 of FIG. 6). A finished joint may be sealed using many different techniques including, for example, over-molding, over-flowing, and the like or combinations thereof.

Figure 8:
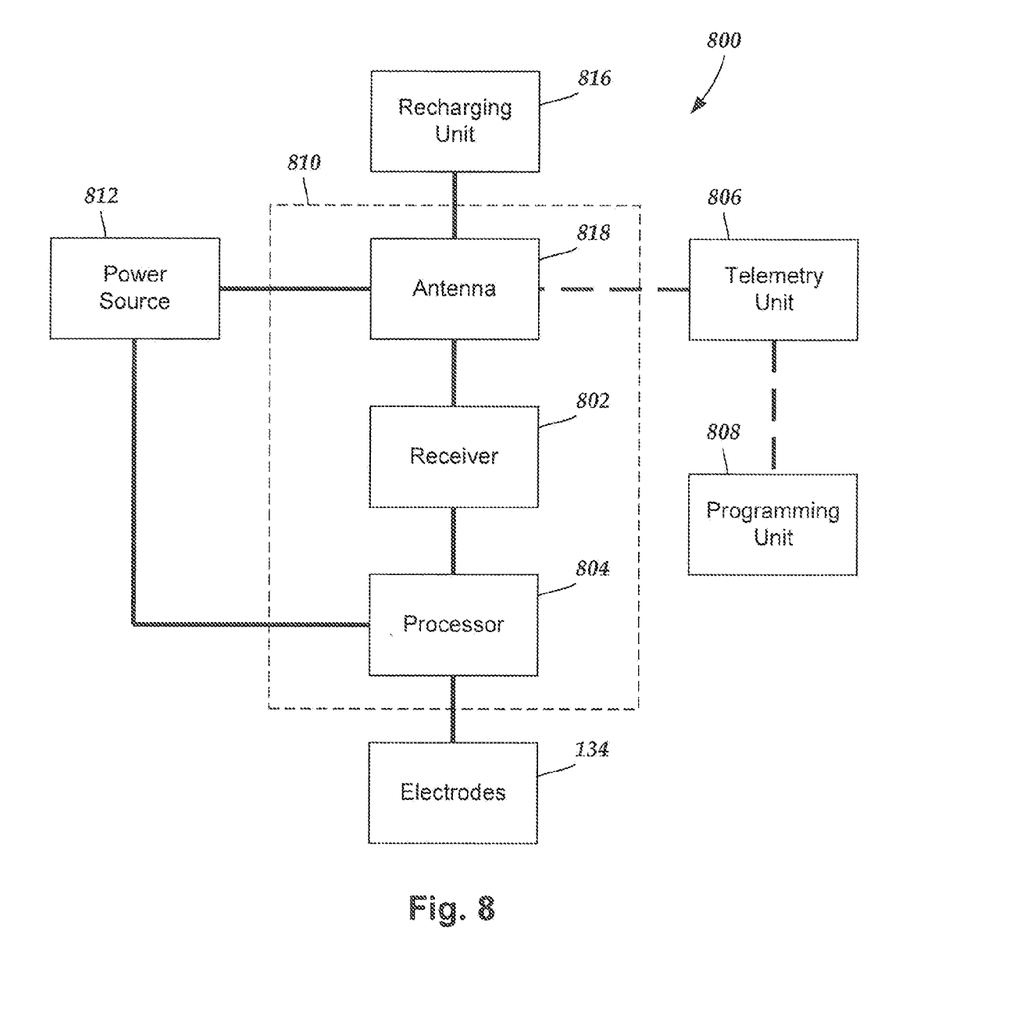
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulating system comprising
   an implantable lead comprising:
     an elongated lead body having proximal end, a distal end, and a longitudinal length, the lead body comprising
       a first lead assembly disposed at one of the proximal end or the distal end of the lead body, the first lead assembly having a tip and an opposing medial end, the first lead assembly comprising a plurality of first external contacts, and at least one conductive wire disposed in the first lead assembly, the at least one conductive wire extending from at least one first external contact towards the medial end of the first lead assembly;
       a medial section with a first end and a second end, the medial section comprising a plurality of conductors extending from the first end to the second end; and
       a first intermediate assembly disposed between the first lead assembly and the first end of the medial section, the first intermediate assembly comprising a plurality of conductive elements, at least one of the conductive elements configured and arranged to electrically couple the at least one conductive wire of the first lead assembly to at least one of the conductors at the first end of the medial section;
     wherein the first lead assembly, the medial section, and the first intermediate assembly maintain an isodiametric profile along the longitudinal length of the lead body;
     wherein the lead body further comprises a second lead assembly electrically coupled to the second end of the medial section, the second lead assembly comprising
       a plurality of second external contacts, and
       at least one conductive wire disposed in the second lead assembly, the at least one conductive wire electrically coupling at least one second external contact disposed on the second lead assembly to at least one conductor at the second end of the medial section;
     wherein the first lead assembly is disposed at the distal end of the lead body and the second lead assembly is disposed at the proximal end of the lead body;
     wherein the plurality of first external contacts comprise a plurality of electrodes and the plurality of second external contacts comprise a plurality of terminals;
   a control module configured and arranged to electrically couple to the proximal end of the lead body, the control module comprising
     a housing, and
     an electronic subassembly disposed in the housing; and
   a connector for receiving the proximal end of the lead body, the connector having a proximal end, a distal end, and a longitudinal length, the connector comprising
     a connector housing defining a port at the distal end of the connector, the port configured and arranged for receiving, the proximal end of the lead body, and
     a plurality of connector contacts disposed in the connector housing, the connector contacts configured and arranged to couple to at least one of the plurality of terminals disposed on the proximal end of the lead body; and
   a lead extension coupling the lead body to the control module, the lead extension comprising
     an elongated lead extension body having a proximal end, a distal end, and a longitudinal length, the lead extension body comprising
     a first lead extension assembly with a tip and an opposing medial end, the first lead extension assembly comprising a plurality of external lead extension contacts, and at least one conductive wire disposed in the first lead extension assembly, the at least one conductive wire extending from at least one external lead extension contact towards the medial end of the first lead extension assembly;
     a medial lead extension section with a first end and a second end, the medial lead extension section comprising a plurality of conductors extending from the first end to the second end; and
     a first intermediate lead extension assembly disposed between the first lead extension assembly and the medial lead extension section, the first intermediate lead extension assembly comprising a plurality of conductive elements, the conductive elements configured and arranged to electrically couple at least one conductive wire of the first lead extension assembly to at least one conductor at the first end of the medial lead extension section.

\* \* \* \* \*